US00PP08695P

United States Patent [19]

Polys

[11] Patent Number: Plant 8,695

[45] Date of Patent: Apr. 19, 1994

[54] CHRYSANTHEMUM PLANT NAMED HONEY CHERIE

[75] Inventor: Susan M. Polys, Salinas, Calif.

[73] Assignee: Yoder Brothers, Inc., Barberton, Ohio

[21] Appl. No.: 62,200

[22] Filed: May 17, 1993

[51] Int. Cl.[5] ..... A01H 5/00

[52] U.S. Cl. ..... Plt./82.2

[58] Field of Search ..... Plt. 82.2, 78

[56] References Cited

U.S. PATENT DOCUMENTS 4,616,099 10/1986 Sparkes ..... 47/58 X

PP. 7468 3/1991 Vanden Berg ..... Plt. 82.2

OTHER PUBLICATIONS

Dowrick, G. J. et al., (1966) "The Induction of Mutations in Chrysanthemum Using X and Gamma Radiation", *Euphytica* 15, pp. 204–210.

Machin, B. J., "Sporting and Irradiation" *The Chrysanthemum Manual* The National Chrysanthemum Society, London, 1979, pp. 329–336.

Broertjes, C., et al., "Chrysanthemum" *Application of Mutation Breeding Methods in the Inprovement of Segetatively Propagated Crops*, Elsevir, N.Y., 1978, pp. 162–174.

Inprovement of Vegetatively Propagated Crops, Elsevier, N.Y., 1978, pp. 162–174 Chan, A. P. (1966) "Chrysanthemum and Rose Mutation Induced by X Rays" *Proceedings* American Society for Host Science, vol. 88, pp. 613–620.

Broertjes, C. (1966) "Mutation Breeding of Chrysanthemums" *Euphytica* 15 pp. 156–162.

Broertjes, C., et al., (1980) "A Mutant of a Mutant of a Mutant of a . . . Irradiation of Progressive Radiation-Induced Mutants in a Mutation-Breeding Programme with Chrysanthemum Morifolium"*Euphytica* 29, pp. 525–530.

Searle, S. A. et al., "Ude of Gamma and X-Rays", *Chrysanthemums the Year Round,* Blandford Press, london, 1968, pp. 27–28.

*Primary Examiner*—James R. Feyrer

*Attorney, Agent, or Firm*—Foley & Lardner

[57] ABSTRACT

A Chrysanthemum plant named Honey Cherie particularly characterized by its flat capitulum form; daisy capitulum type; soft honey-bronze ray floret color; diameter across face of capitulum of 38 to 41 mm when fully opened, when grown as a pinched spray pot mum; very floriferous, with excellent display of many small flowers; photoperiodic flowering response of 52 days after start of short days; plant height, with 13 to 14 long days after sticking unrooted cuttings, and with 0 to 1 applications of 2500 ppm B-9 SP, ranges from 20 to 25 cm when grown as a pinched pot mum with 4 cuttings in a 15 cm pot; branching pattern is spreading and prolific, each plant having 7 to 8 laterals after pinch; and recommended as a spray pot mum.

2 Drawing Sheets

The present invention comprises a new and distinct cultivar of Chrysanthemum, botanically known as *Dendranthema grandiflora*, and referred to by the cultivar name Honey Cherie.

Honey Cherie, identified as 4238 (89-114E03) is a product of a mutation induction program. The new cultivar was discovered and selected by Susan M. Polys on Jan. 13, 1992, in a controlled environment in Salinas, Calif., as one flowering plant within a flowering block established as rooted cuttings from stock plants which had been exposed as unrooted cuttings to an X-ray source of 2000 rads in Fort Myers, Fla., on May 9, 1991. The irradiated parent cultivar was an unnamed proprietary seeding identified as 4207 (89-114003), and described as a daisy spray pot mum with a flat capitulum form; a very light pink ray floret color; diameter across face of capitulum of 32 to 48 mm when fully opened, flowering response period of 49 to 56 days after start of short days; plant height of 18 to 25 cm with 0 to 1 applications of 2500 ppm B-9 SP when grown as a pinched pot mum in a 15 cm pot; and spreading and prolific branching pattern, with 6 to 8 laterals after pinch. The parent cultivar has not been sold or offered for sale, or otherwise publicly disclosed.

The irradiation program resulting in Honey Cherie has as its primary objective the expansion of the color range of the parent seedling 4207, with the ray floret color of the parent considered to be too light for commercial introduction, while all other characteristics of the parent were considered to be excellent. The irradiation program comprised irradiating cuttings of the parent cultivar at irradiation levels of 1500, 1750 and 200 rads. A total of 2470 cuttings harvested from a total of 225 irradiated plants were planted on Sep. 9, 1991. of these, 37 initial selections were made, which selections were then revegetated and reflowered. Three consecutive flowering resulted in discarding 32 of the original 37 selectionson Jul. 1, 1992. Five selections were retained and reflowered again, ultimately resulting in the descision to indtroduce all remaining selections as Honey Chereie, Dark Cherie, Soft Cherie, Sunny Cherie and Sweet Cherie. Applications are prending for the other induced mutations.

The first act of asexual reproduction of Honey Cherie was accomplished when vegetative cuttings were taken from the initial selection to Mar. 1992 in a controlled environment in Salinas, Calif., by technicians working under supervision of Susan M. Polys.

Horticultural examination of controlled flowerings of successive planting has shown that the unique combination of characteristics as herein disclosed for Honey Cherie are firmly fixed and are retained through successive generations of asexual reproduction.

Honey Cherie has not been observed under all possible environemtnal conditions. The phenotype may vary significantly with variations in environment such as temperature, light intensity and daylenght, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Honey Cherie, which, in combinations, distinguish this Chrysanthemum as a new and distinct cultivar:

1. Flat capitulum form.
2. Daisy capitulum type.
3. Soft, honey-bronze ray floret color.
4. Diameter across face of capitulum of 38 to 41 mm when fully opened, when grown as a pinched spray pot mum.
5. Very floriferous, with excellent display of many small flowers.
6. Photoperiodic flowering response of 52 days after start of short days.
7. Plant height, with 13 to 14 long days after sticking unrooted cuttings and with 0 to 1 applications of 2500 ppm B-9 SP, ranges from 20 to 25 cm when grown as a pinched pot mum with 4 cuttings in a 15 cm pot.
8. Branching pattern is spreading and prolific, each plant having 7 to 8 laterals after pinch.
9. Recommended as a spray pot mum.

The accompanying photographic drawings show typical inflorescence and leaf characteristics of Honey Cherie, with the colors being as nearly true as possible with illustrations of this type.

Sheet 1 is a color photogrpah of a potted mum of Heny Cherie, with 4 cuttings in a 15 cm pot.

Sheet 2 is a black and white photograph showing the upper and under sides of the leaves of the Cherie series at three stages of development (mature, intermediate and immature). In sheet 2 a measuring tape in centimeters has been added.

Of the commercial cultivars known to the inventor, the most similar in comparison to Honey Cherie is the cultivar identified as Alouette, disclosed in U.S. Plant Pat. No. 7,468, Reference is made to attached Chart A, which compares certain characteristics of Honey Cherie with the same characteristics as Alouette.

Similar traits are capitulum form and type, branching pattern, and recommendation as a spray top mum. Honey Cherie has soft honey-bronze ray floret color, while Alouette has has a yellow ray floret color with bronzing buds and a bronze overcast of the underside of the ray florets. Honey Cherie has a larger diameter of capitulum than Alouette, and has a slower flowering response when grown side by side. The range of measurements of Honey Cherie is much wider than the range of measurements of Honey Cherie, based on the fact that Alouette has been tested for many years, while Honey Cherie has been tested for only nine months at the time of the application.

When compared with the parent seedling, all traits of Honey Cherie are similar to those of the parent, except for the color of the ray florets. When comparing the description of Honey Cherie with the description of the parent, it is evident that the parent seedling has much wider range of measurements than Honey Cherie. This is also based on evaluations over a long time period for the parent in comparison with the short time period that Honey cherie has been tested.

In the following description color references are made to The Royal Horticultural Society Colour Chart. The color values were determined on plant material grown as a pinched spray pot mum in Salinas, Calif. on Feb. 23, 1993.

Classification:

*Botanical.*—*Dendranthema grandiflora* cv Honey Cherie.

*Commercial.*-Flat daisy spray pot mum.

INFLORESCENE

A. Capitulum:

*Form.*—Flat.

*Type.*—Daisy.

*Diameter across face.*—38 to 41 mm when fully opened.

B. Corolla of ray florets:

*Color (general tonality from a distance of three meters).*—Soft honey-bronze.

*Color (upper surface).*—12B, overlaid and slightly streaked with 163B.

*Color (under surface).*—16B, overlaid with 163B. The under surface is more strongly overlaid than the upper surface.

*Shape.*—*Straight, oblong,* slightly ribbed.

C. Corolla of disc florest:

*Color (mature).*—14B. *Color (immature).*—14B, center overlaid with 144B.

D. Reproductive organs:

*Androecium.*—Present on disc florets only; moderate pollen.

*Gynoecium.*—Present on both ray and disc florets.

PLANT

A. General apperance:

*Height.*—20 to 25 cm when grown as a pinched pot mum with 13 to 14 long days prior to start of short days, with 0 to 1 applications of 2500 ppm B-9 SP.

*Branching pattern.*—Spreading and prolific, with 7 to 8 laterals after pinch.

B. Foliage:

*Color (upper surface).*—147A.

*Color (under surface).*—147B.

*Shape.*—See photograph.

CHART A

COMPARISONS MADE OF PLANTS GROWN AS PINCHED SPRAY POT MUMS IN SALINAS, CALIFORNIA

| CULTIVAR | HONEY CHERIE | ALDVETTE |
|---|---|---|
| Ray floret color | Soft honey-bronze | Yellow with bronze buds and underside |
| Capitulum form and type | Flat Daisy | Flat Daisy |
| Diameter across face of capitulum | 38 to 41 mm | 32 to 38 mm |
| Flowering Response | 52 days | 45 to 52 days |
| Plant height with 13 to 14 long days | 20 to 25 cm | 20 to 28 cm |
| Branching pattern | Spreading 7 to 8 laterals | Spreading 6 to 8 laterals |
| Recommended as | Spray pot mum | Spray pot mum |

I claim:

1. A new and distinct Chrysanthemum plant named Honey Cherie, as described and illustrated.

* * * * *

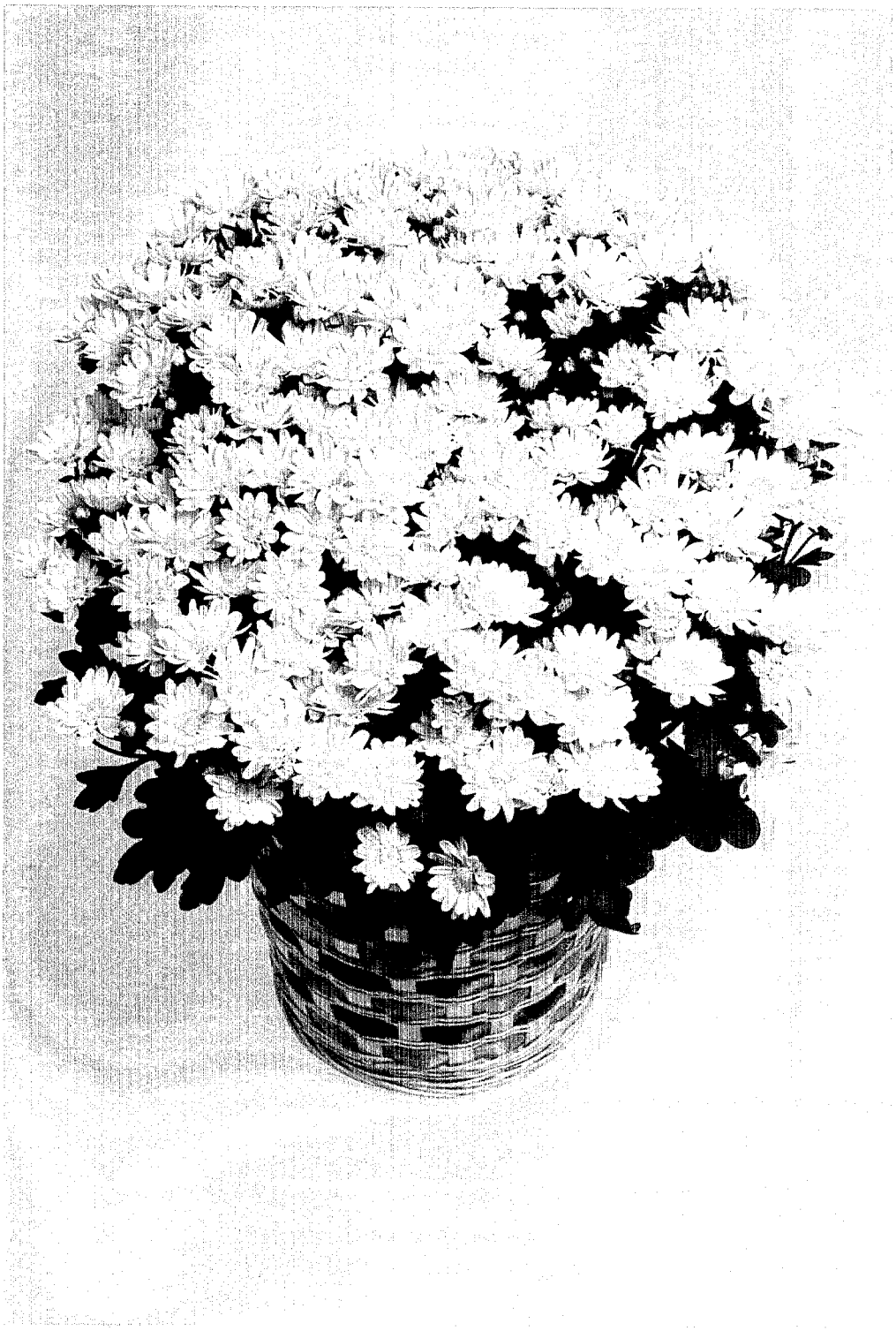

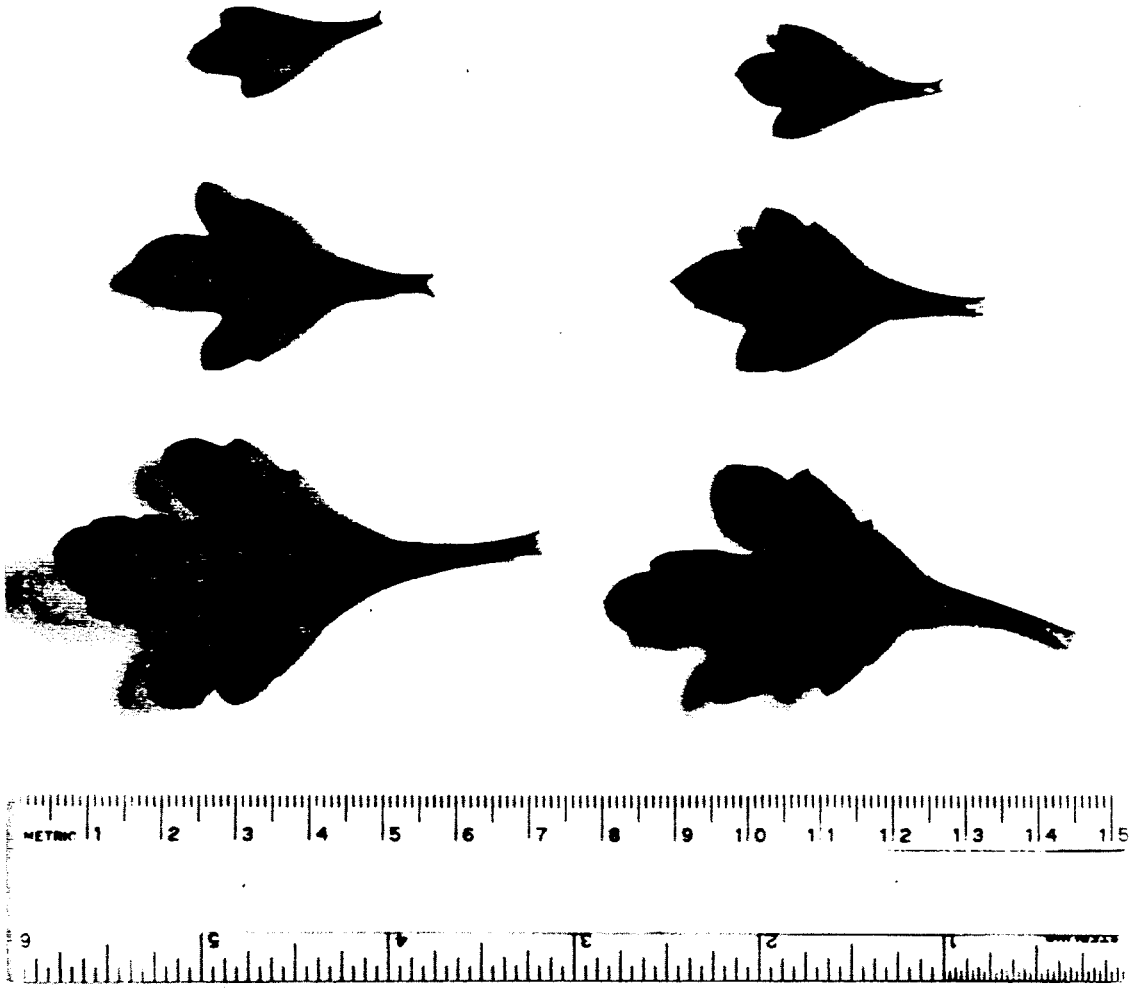
METRIC 1 2 3 4 5 6 7 8 9 10 11 12 13 14 15

UNITED STATES PATENT AND TRADEMARK OFFICE

CERTIFICATE OF CORRECTION

PATENT NO. : PP 8,695

DATED : April 19, 1994

INVENTOR(S) : Susan M. POLYS

BEST AVAILABLE COPY

It is certified that error appears in the above-indentified patent and that said Letters Patent is hereby corrected as shown below:

On the title page, Item [56] References Cited, under "U.S. PATENT DOCUMENTS", "Vanden Berg" should read --VandenBerg--; under "OTHER PUBLICATIONS", "Segetatively" should read --Vegetatively--; "Host Science" should read --Hort Science--.

Column 2, line 3, "200" should read --2000--;

line 9, "selectionson" should read --selections on--;

UNITED STATES PATENT AND TRADEMARK OFFICE

CERTIFICATE OF CORRECTION

PATENT NO. : PP 8,695
DATED : April 19, 1994
INVENTOR(S) : Susan M. POLYS

BEST AVAILABLE COPY

It is certified that error appears in the above-indentified patent and that said Letters Patent is hereby corrected as shown below:

line 11, "indtroduce" should read --introduce--;

line 13, "prending" should read --pending--;

line 17, "to Mar." should read --in March--;

line 27, "environemtnal" should read --environmental--.

Column 3, line 1, "daylenght" should read --daylength--;

line 32, "photogrpah" should read --photograph--;

line 33, "Heny Cherie" should read --Honey Cherie--;

UNITED STATES PATENT AND TRADEMARK OFFICE

CERTIFICATE OF CORRECTION

PATENT NO. : PP 8,695

DATED : April 19, 1994

INVENTOR(S) : Susan M. POLYS

BEST AVAILABLE COPY

It is certified that error appears in the above-indentified patent and that said Letters Patent is hereby corrected as shown below:

line 47, "top mum" should read --pot mum--;

line 54, "Honey Cherie" should read --Alouette--;

line 67, "cherie" should read --Cherie--;

Column 4, line 51, "ALDVETTE" should read --ALOUETTE--.

Signed and Sealed this

Twenty-second Day of November, 1994

*Attest:*

Bruce Lehman

BRUCE LEHMAN

*Attesting Officer*

*Commissioner of Patents and Trademarks*